(12) United States Patent
Fujimoto et al.

(10) Patent No.: US 11,033,246 B2
(45) Date of Patent: Jun. 15, 2021

(54) RADIOGRAPHIC IMAGING APPARATUS AND IMAGING METHOD

(71) Applicant: General Electric Company, Schenectady, NY (US)

(72) Inventors: Ryosuke Fujimoto, Tokyo (JP); Shigeru Chikamatsu, Tokyo (JP)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 16/020,107

(22) Filed: Jun. 27, 2018

(65) Prior Publication Data

US 2018/0372657 A1   Dec. 27, 2018

(30) Foreign Application Priority Data

Jun. 27, 2017 (JP) .............................. JP2017-124771

(51) Int. Cl.
*A61B 6/03* (2006.01)
*A61B 6/00* (2006.01)
(Continued)

(52) U.S. Cl.
CPC .............. *A61B 6/545* (2013.01); *A61B 6/032* (2013.01); *A61B 6/06* (2013.01); *A61B 6/488* (2013.01);
(Continued)

(58) Field of Classification Search
CPC ......... A61B 6/032; A61B 6/04; A61B 6/0407; A61B 6/0457; A61B 6/06; A61B 6/40;
(Continued)

(56) References Cited

U.S. PATENT DOCUMENTS 5,825,843 A * 10/1998 Kobayashi ............. A61B 6/102
378/20
5,949,811 A * 9/1999 Baba .................... A61B 6/4225
378/108
(Continued)

FOREIGN PATENT DOCUMENTS

JP  1998071141  3/1998
JP  3847101  12/2002
(Continued)

OTHER PUBLICATIONS

English translation of JP5314692 at EPO Patent Translate on Sep. 28, 2019.*
(Continued)

*Primary Examiner* — Allen C. Ho (57) ABSTRACT

A radiographic imaging apparatus for capturing a radiographic image by emitting radiation onto an object to be imaged comprises: a storage device for storing therein imaging conditions for a radiographic image; a control device for controlling several sections in the radiographic imaging apparatus to perform preparation for the image capture based on the imaging conditions loaded from the storage device; and an input device for accepting an input by an operator, wherein the input device is configured to accept an input of a result of a decision by the operator as to whether or not to modify the imaging conditions loaded from the storage device, and the control device controls several sections in the radiographic imaging apparatus to start the preparation for the image capture before the input device accepts the input of the result of the decision.

20 Claims, 3 Drawing Sheets

(51) Int. Cl.
*G01N 23/083* (2018.01)
*G01N 23/046* (2018.01)
*A61B 6/06* (2006.01)

(52) U.S. Cl.
CPC .............. *A61B 6/5229* (2013.01); *A61B 6/54* (2013.01); *A61B 6/542* (2013.01); *G01N 23/046* (2013.01); *G01N 23/083* (2013.01); *A61B 6/4435* (2013.01); *A61B 6/467* (2013.01)

(58) Field of Classification Search
CPC ....... A61B 6/4035; A61B 6/4042; A61B 6/42; A61B 6/4208; A61B 6/4233; A61B 6/46; A61B 6/467; A61B 6/469; A61B 6/54; A61B 6/542; A61B 6/545; G21K 1/02; G21K 1/04; G21K 1/043; G21K 1/046; H01J 35/06; H01J 35/10
USPC ....... 378/16, 20, 62, 19, 125, 134, 144, 147, 378/150–153, 156–159
See application file for complete search history.

(56) References Cited

U.S. PATENT DOCUMENTS

| | | | | |
|---|---|---|---|---|
| 6,125,167 | A * | 9/2000 | Morgan | H01J 35/10 378/121 |
| 6,463,121 | B1 * | 10/2002 | Milnes | A61B 6/4482 378/62 |
| 6,480,572 | B2 * | 11/2002 | Harris | H01J 35/06 378/136 |
| 6,707,876 | B2 | 3/2004 | Tanigawa | |
| 7,082,189 | B2 * | 7/2006 | Yahata | A61B 6/06 378/156 |
| 7,113,569 | B2 * | 9/2006 | Okumura | A61B 6/032 378/150 |
| 7,120,222 | B2 * | 10/2006 | Hoffman | A61B 6/032 378/5 |
| 7,149,277 | B2 * | 12/2006 | Tanigawa | A61B 6/032 378/18 |
| 7,254,216 | B2 * | 8/2007 | Thandiackal | A61B 6/032 378/157 |
| 7,308,073 | B2 * | 12/2007 | Tkaczyk | G21K 1/10 378/156 |
| 7,336,769 | B2 * | 2/2008 | Arenson | G21K 1/04 378/159 |
| 7,382,853 | B2 * | 6/2008 | Arenson | A61B 6/4241 378/19 |
| 7,522,701 | B2 * | 4/2009 | Jensen | A61B 6/481 378/162 |
| 7,881,425 | B2 * | 2/2011 | Vermilyea | H01J 35/10 378/132 |
| 8,649,480 | B2 * | 2/2014 | Yoshida | A61B 6/032 378/16 |
| 8,660,235 | B2 * | 2/2014 | Koehler | A61B 6/032 378/4 |
| 8,761,333 | B2 * | 6/2014 | Ikhlef | A61B 6/032 29/428 |
| 8,942,341 | B2 * | 1/2015 | Hsieh | A61B 6/032 378/16 |
| 8,953,746 | B2 * | 2/2015 | Roshi | H01J 35/06 378/125 |
| 9,142,381 | B2 * | 9/2015 | Onken | H01J 35/045 |
| 9,274,066 | B2 * | 3/2016 | Ji | G01N 23/046 |
| 9,826,952 | B2 * | 11/2017 | Nakazawa | A61B 6/5217 |
| 9,888,902 | B2 * | 2/2018 | Ueki | A61B 6/032 |
| 9,901,314 | B2 * | 2/2018 | Koehler | A61B 6/4035 |
| 9,904,767 | B2 * | 2/2018 | Desai | A61B 6/548 |
| 9,980,690 | B2 * | 5/2018 | Muroi | A61B 6/463 |
| 10,045,755 | B2 * | 8/2018 | Meetz | A61B 6/503 |
| 10,083,528 | B2 * | 9/2018 | Kim | G01R 33/20 |
| 10,085,698 | B2 * | 10/2018 | Fan | A61B 6/488 |
| 10,111,639 | B2 * | 10/2018 | Karahashi | A61B 6/542 |
| 10,210,633 | B2 * | 2/2019 | Yamakawa | A61B 6/5258 |
| 10,218,750 | B2 * | 2/2019 | Gotnam | H04L 65/40 |
| 10,219,763 | B2 * | 3/2019 | Kojima | A61B 6/542 |
| 10,289,953 | B2 * | 5/2019 | Lee | G06N 5/04 |
| 10,292,668 | B2 * | 5/2019 | Konno | A61B 6/585 |
| 10,297,414 | B2 * | 5/2019 | Meiler | H01J 35/14 |
| 10,342,503 | B2 * | 7/2019 | Kobayashi | A61B 6/5282 |
| 10,368,825 | B2 * | 8/2019 | Crotty | A61B 6/488 |
| 10,383,583 | B2 * | 8/2019 | Tomomura | A61B 6/545 |
| 10,383,590 | B2 * | 8/2019 | Vaz | A61B 6/501 |
| 10,383,593 | B2 * | 8/2019 | Jung | A61B 6/461 |
| 10,383,594 | B2 * | 8/2019 | Wang | A61B 6/545 |
| 10,398,400 | B2 * | 9/2019 | Kim | A61B 6/4291 |
| 10,413,261 | B2 * | 9/2019 | Xu | G06T 7/0012 |
| 10,485,503 | B2 * | 11/2019 | Schaefer | A61B 6/5205 |
| 10,497,152 | B2 * | 12/2019 | Miyazaki | A61B 6/032 |
| 10,540,764 | B2 * | 1/2020 | Tsukagoshi | A61B 6/032 |
| 10,667,767 | B2 * | 6/2020 | Stevens | A61B 6/035 |
| 10,835,197 | B2 * | 11/2020 | Goto | A61B 6/545 |
| 2002/0191737 | A1 | 12/2002 | Tanigawa | |
| 2015/0313569 | A1 * | 11/2015 | Stevens | A61B 6/032 378/8 |

FOREIGN PATENT DOCUMENTS

| | | |
|---|---|---|
| JP | 2009285147 A | 12/2009 |
| JP | 20090014601 A | 8/2010 |
| JP | 5314692 | 2/2012 |
| JP | 20170861011 A | 7/2018 |

OTHER PUBLICATIONS

English translation of JP2002-345803 A at EPO Patent Translate on Sep. 28, 2019.*

Japanese application No. 2017-124771 filed Jun. 27, 2017—Notice of Preliminary Rejection dated Oct. 27, 2020; 13 pages.

* cited by examiner

RADIOGRAPHIC IMAGING APPARATUS AND IMAGING METHOD

FIELD OF THE INVENTION

The present invention relates to a radiographic imaging apparatus and an imaging method for producing a radiographic image by emitting radiation onto an object to be imaged.

BACKGROUND OF THE INVENTION

For example, in an X-ray CT apparatus (X-ray Computed Tomography System), which is an example of a radiographic imaging apparatus, capture of an X-ray CT image, which is an example of a radiographic image, is achieved according to a procedure as follows, for example. First, an operator selects an imaging protocol depending upon the body part to be imaged or the symptom, whereupon imaging conditions according to the imaging protocol are loaded. In the case that the loaded imaging conditions have to be modified, the operator performs an input for modifying the imaging conditions and confirming them. In the case, on the other hand, that the loaded imaging conditions do not have to be modified, the operator performs an input for confirming the imaging conditions. Once the imaging conditions have been confirmed, preparation for image capture is started based on the confirmed imaging conditions. When the preparation for image capture is completed, the operator performs an input for starting an X-ray scan.

The preparation for image capture involves bringing hardware constituting the X-ray CT apparatus to a state ready to perform image capture. For example, the preparation for image capture comprises rotating an anode in an X-ray tube, and rotating a gantry.

BRIEF DESCRIPTION OF THE INVENTION

In CT examinations, it is desired by management, and by radiologists as well, to reduce the examination time per medical patient as much as possible because this may increase the number of patients that can be examined per CT machine per day, or reduce the working time of a radiologist. At the same time, reduction of the examination time may lead to mitigation of patient stress.

The inventors have intensively studied the imaging flow described above, intending to improve examination efficiency by reduction of the examination time. Since some time is required in preparation for image capture in the imaging flow described above, it takes an amount of time after the operator has confirmed imaging conditions and before image capture is ready, which results in a wait time for the operator. Accordingly, the inventors have focused upon reduction of the time from an input of a result of a decision by the operator as to whether or not to modify imaging conditions to when image capture is ready to start.

The reason why the start of preparation for image capture is arranged to follow the operator's input for confirming imaging conditions is that the loaded imaging conditions are possibly modified by the operator. Such modification on the loaded imaging conditions by the operator, however, is not very frequently encountered. Accordingly, the inventors have focused upon this issue, and finally solved the problem of reducing the time from an input of a result of a decision by the operator as to whether or not to modify imaging conditions to when image capture is ready to start.

The invention, in one aspect, made to solve the aforementioned problem is a radiographic imaging apparatus for capturing a radiographic image by emitting radiation onto an object to be imaged, comprising: a storage device for storing therein imaging conditions for said radiographic image; a control device for controlling several sections in said radiographic imaging apparatus to perform preparation for said image capture based on said imaging conditions loaded from said storage device; and an input device for accepting an input by an operator, wherein said input device is configured to accept an input of a result of a decision by the operator as to whether or not to modify said imaging conditions loaded from said storage device, and said control device controls several sections in said radiographic imaging apparatus to start said preparation for said image capture before said input device accepts said input of the result of the decision.

The invention, in another aspect, is the radiographic imaging apparatus of the invention in the one aspect described above, wherein: said input of the result of the decision by the operator that said input device accepts after the start of said preparation for said image capture includes an input by the operator modifying said imaging conditions loaded from said storage device, and once said input device has accepted said input of modifying said imaging conditions, said control device controls several sections in said radiographic imaging apparatus to perform said preparation for said image capture again based on the modified imaging conditions.

According to the invention in the one aspect described above, the control device is configured to control several sections in the radiographic imaging apparatus to perform, before the input of the result of the decision by the operator as to whether or not to modify the imaging conditions loaded from the storage device is performed, the preparation for the image capture based on the imaging conditions loaded from the storage device. Hence, time-consuming preparation for image capture can be started in an earlier phase, thus reducing the operator's wait time from the input of the result of the decision by the operator for the imaging conditions to when image capture is ready to start.

According to the invention in the other aspect described above, the input device is configured to, in the case that the imaging conditions loaded from the storage device have to be modified, accept an input from the operator modifying the imaging conditions after the preparation for image capture is started. Therefore, although the preparation for the image capture is started before the input of the result of the decision for the imaging conditions, the operator can set desired imaging conditions.

BRIEF DESCRIPTION OF THE DRAWINGS

The present invention can be better understood in light of the following description of embodiments of the present invention with reference to the accompanying drawings, in which.

DETAILED DESCRIPTION OF THE INVENTION

Now an embodiment of the invention will be described hereinbelow. It should be noted that the invention is not limited thereto.

Figure 1:
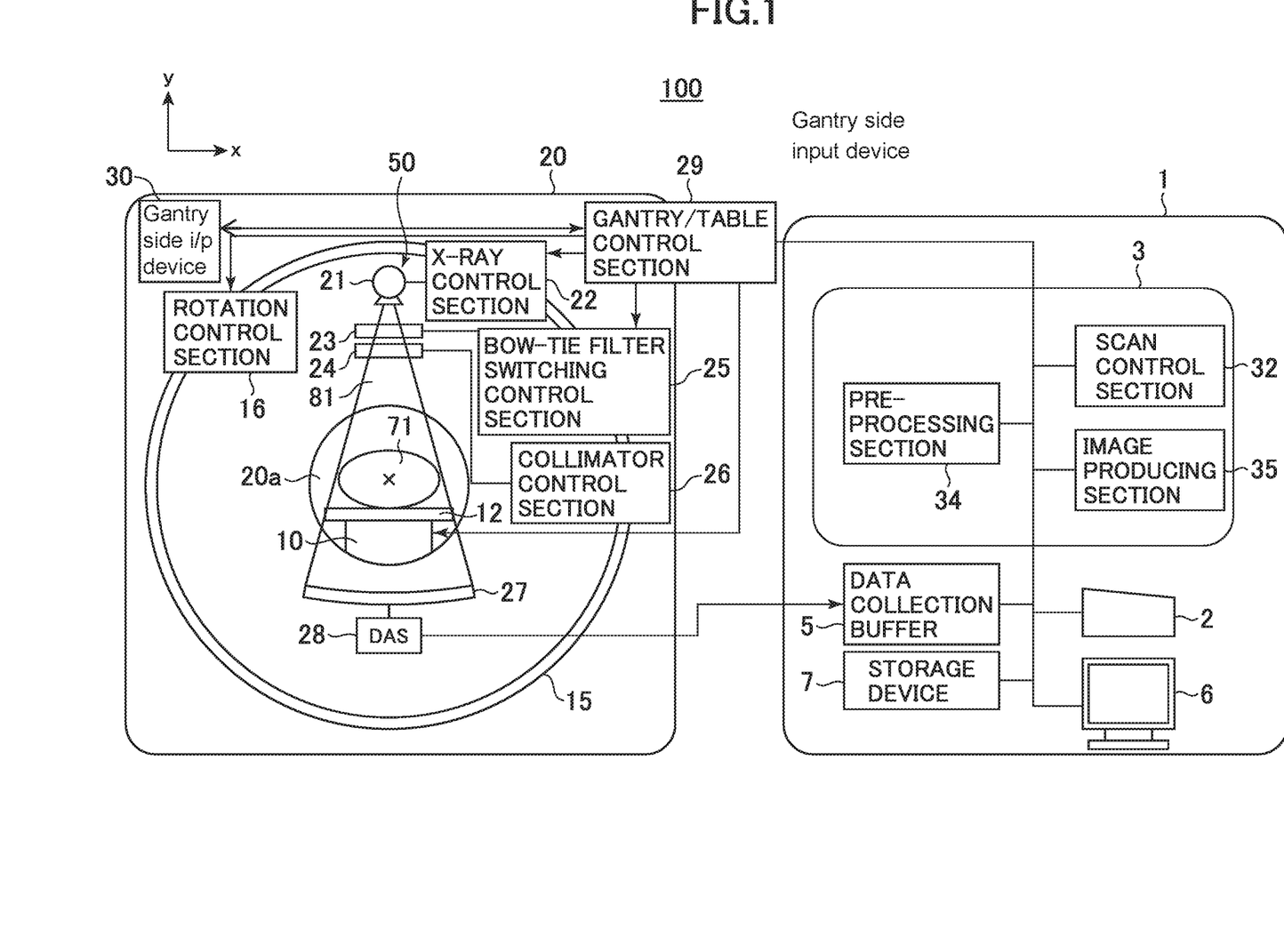
FIG. 1 illustrates a diagram schematically showing a configuration of an X-ray CT apparatus in accordance with an embodiment of the present invention.

In FIG. 1 is shown an X-ray CT apparatus 100, which is an exemplary embodiment of the radiographic imaging apparatus in the present invention. The X-ray CT apparatus 100 comprises an operation console 1, an imaging table 10, and a scan gantry 20.

The operation console 1 has a configuration as a computer. Specifically, the operation console 1 comprises an input device 2 for accepting an input by an operator, such as buttons, a keyboard, and a pointing device, a control device 3 for executing scan control processing, pre-processing, image production processing, etc., and a data collection buffer 5 for collecting X-ray detector data collected in the scan gantry 20. The operation console 1 further comprises a monitor 6 for displaying an X-ray CT image produced by the image production processing, etc., and a storage device 7 for storing therein programs, X-ray detector data, X-ray projection data (projection data), X-ray CT images, etc.

In the storage device 7 are also stored imaging conditions (scan parameters) for an X-ray CT image. The storage device 7 is an exemplary embodiment of the storage device in the present invention. The storage device 7 includes non-transitory storage media and transitory storage media. The non-transitory storage media are non-volatile storage media, such as HDD (Hard Disk Drive), and ROM (Read Only Memory), for example. The non-transitory storage media may include portable storage media, such as CD (Compact Disk) and DVD (Digital Versatile Disk). Programs executed by the control device 3 are stored in the non-transitory storage media, as will be discussed later.

The transitory storage media are volatile storage media, such as RAM (Random Access Memory).

The imaging table 10 comprises a cradle 12 for laying thereon a subject 71 to be examined, which is an object to be imaged, to carry the subject 71 into/out of a bore 20 a in the scan gantry 20, which will be discussed later. The cradle 12 is vertically moved and horizontally translated by a motor incorporated in the imaging table 10. The imaging table 10 is an exemplary embodiment of an imaging table in the present invention.

The scan gantry 20 has the bore 20a in which the subject 71 is placed. The subject 71 is carried into the bore 20a by the cradle 12 to be placed within the bore 20a. The scan gantry 20 is an exemplary embodiment of a gantry in the present invention.

In the scan gantry 20 is contained an X-ray emitting module 50. The X-ray emitting module 50 comprises an X-ray tube 21, an X-ray control section 22 for controlling X-ray tube voltage, X-ray emission timing, etc. in the X-ray tube 21, a bow-tie filter module 23 having a plurality of bow-tie filters, and a collimator 24 having an aperture for limiting a range of impingement of X-rays emitted from the X-ray tube 21. The X-ray emitting module 50 is an exemplary embodiment of a radiation emitting module in the present invention.

The scan gantry 20 moreover has a bow-tie filter switching control section 25 for performing switching control of the plurality of bow-tie filters, a collimator control section 26 for controlling the aperture of the collimator 24, an X-ray detector 27 for detecting the X-rays emitted from the X-ray tube 21, and a data collection apparatus (DAS: Data Acquisition System) 28 for collecting X-ray detector data (also referred to as raw data) from an output of the X-ray detector 27.

The scan gantry 20 further has a gantry rotating section 15 for holding the X-ray tube 21, bow-tie filter module 23, collimator 24, and X-ray detector 27 and rotating them around a body axis of the subject 71, and a rotation control section 16 for controlling the gantry rotating section 15. Furthermore, the scan gantry 20 has a gantry/table control section 29 for communicating control signals between the operation console 1, and the X-ray control section 22, rotation control section 16, bow-tie filter switching control section 25, collimator control section 26, imaging table 10, etc. The scan gantry 20 also has a gantry-side input device 30 for accepting an input by the operator.

The gantry-side input device 30 may be configured to include buttons and a touch panel. The gantry-side input device 30 communicates signals with the gantry/table control section 29.

Figure 2:
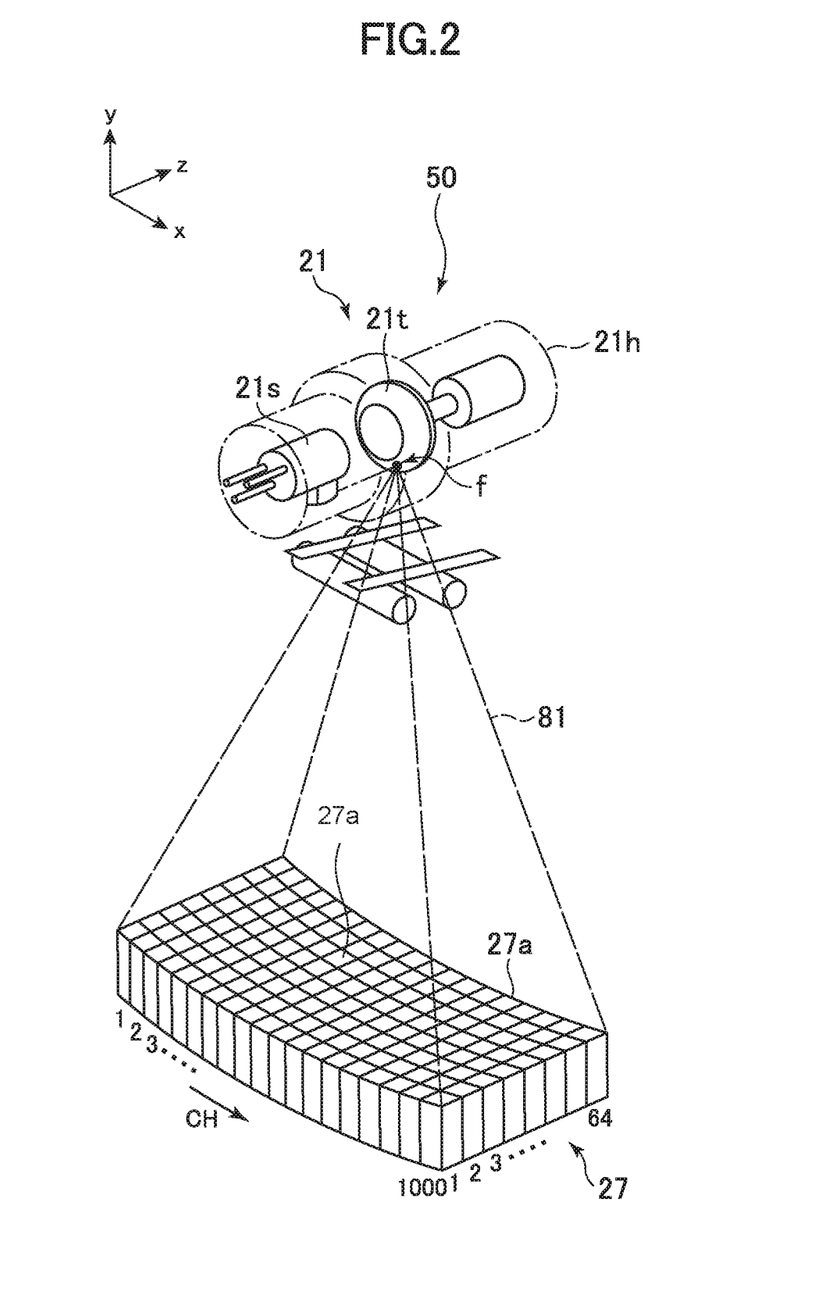
FIG. 2 illustrates a schematic diagram showing a configuration of an X-ray emitting module and an X-ray detector in the X-ray CT apparatus shown in FIG. 1.

FIG. 2 is a diagram showing a configuration of the main portion of the X-ray emitting module 50 and X-ray detector 27. As used herein, the vertical direction is defined as y-axis direction, a direction of carriage of the imaging table 10 (which ordinarily matches a direction of the thickness of an X-ray beam 81 or a direction of the body axis of the subject 71) is defined as z-axis direction, and a direction (channel direction) perpendicular to the y- and z-axis directions is defined as x-axis direction.

These components are supported by a given substructure of the gantry rotating section 15 to keep a positional relationship as shown. Specifically, the X-ray emitting module 50 and X-ray detector 27 are disposed to face each other across the bore 20a, and are configured to be rotatable around the subject 71 placed in the bore 20a while keeping the mutual positional relationship. Moreover, the X-ray tube 21 is configured so that X-rays are emitted therefrom onto the subject 71 placed in the bore 20a.

X-rays emitted from the X-ray tube 21 pass through the aperture formed by the collimator 24, whereby a fan-shaped X-ray beam 81 having a specific thickness (cone angle) and span (fan angle) is formed. The collimator 24 is an exemplary embodiment of the collimator in the present invention.

The X-ray tube 21 has a structure in which a cathode sleeve 21s incorporating therein a focusing electrode and a cathode filament, and a rotatable target electrode 21t are contained in a housing 21h, and it generates X-rays emanating from an X-ray focus F. Although the specific configuration of the cathode filament is not particularly shown, it may be provided with a plurality of cathode filaments for selection. The configuration of the X-ray tube 21 is an example, and is not limited to the structure in which only the rotatable target electrode 21t is rotated. The X-ray tube 21 is an exemplary embodiment of the radiation source in the present invention. The rotatable target electrode 21t is an exemplary embodiment of the members constituting the X-ray tube 21 in the present invention. The cathode filament(s) incorporated in the cathode sleeve 21s is an exemplary embodiment of the filament in the present invention.

The X-ray emitting module 50 comprises the bow-tie filter module 23, which is shown only in FIG. 1 and not shown in FIG. 2. The bow-tie filter module 23 comprises a plurality of bow-tie filters. The bow-tie filters are intended for spatially optimizing the X-ray intensity to provide uniform X-ray absorption between a central portion and end portions of the subject 71 in a slice plane. The bow-tie filter module 23 comprises bow-tie filters of different sizes as the plurality of bow-tie filters, and the bow-tie filter switches to one for use in a scan according to the size of a body part to be scanned. For example, there are provided three sizes of bow-tie filters of [Large], [Medium], and [Small], and when the body part to be scanned is an adult chest, the bow-tie filter switches to the [Large] one, when the body part is a pediatric chest, it switches to the [Medium] one, and when the body part is a pediatric head, it switches to the [Small] one. The kind of the bow-tie filter for use in a scan is one of imaging conditions. The bow-tie filter(s) constituting the bow-tie filter module 23 is an exemplary embodiment of a bow-tie filter in the present invention.

The X-ray detector 27 is what is generally called a multi-row X-ray detector in which a plural number of, for example, a thousand, X-ray detector elements 27a are arranged in a channel direction CH (a direction of the span of the X-ray beam 81) to form a detector element row, and a plural number of, for example, sixty four, detector element rows are disposed in the z-axis direction (a direction of the thickness of the X-ray beam 81). The sixty-four detector element rows here, however, represent an example, and the present invention is not limited thereto. The X-ray detector 27 detects the X-ray beam 81 passing through the subject 71 placed in the bore 20a by the plurality of X-ray detector elements 27a. The X-ray detector element 27a is constructed as what is generally called a solid-state detector by, for example, a combination of scintillators and photodiodes. The X-ray detector 27 is an exemplary embodiment of a radiation detector in the present invention.

The control device 3 has a scan control section 32, a pre-processing section 34, and an image producing section 35. The control device 3 is a processor, such as a CPU (Central Processing Unit), for example. The control device 3 loads and executes programs stored in the storage device 7 to thereby achieve functions of the scan control section 32, pre-processing section 34, and image producing section 35. The programs represent an exemplary embodiment of the control program in accordance with the present invention.

The control device 3 controls the gantry/table control section 29 to perform X-ray image capture. It also controls the gantry/table control section 29 to perform preparation for the X-ray image capture. The control device 3 controls the gantry/table control section 29 based on the imaging conditions loaded from the storage device 7. Details thereof will be discussed later. The control device 3 and gantry/table control section 29 represent an exemplary embodiment of a control device in the present invention.

An operation of the X-ray CT apparatus 100 in the present embodiment will be described hereinbelow with reference to the flow chart in FIG. 3. The X-ray CT apparatus 100 captures an X-ray image, which is an example of the radiographic image in the present invention. Specifically, first, at Step S1, the operator uses the input device 2 to set a scan protocol. For example, the operator sets a scan protocol by selecting one of a plurality of scan protocols depending upon the body part to be examined in the subject 71 and the symptom of the subject 71. An input of setting of a scan protocol by the operator at the input device 2 is an example of the input of an intention of performing capture of a radiographic image on the object to be imaged in the present invention.

The scan protocols include imaging conditions, such as, for example, the body part to be imaged, the range for a scout scan, distinction between pediatric and adult patients, distinction between head-first/feet-first, the tube voltage for the X-ray tube 21, and the reconstruction function. One scan protocol may include a plurality of shots of image capture. The image capture includes a scout scan and a main scan.

At Step S2, the control device 3 loads imaging conditions according to the scan protocol set at Step S1 from the storage device 7.

At Step S3, after laying the subject 71 on the cradle 12, the operator performs registration. For example, the operator registers any one of landmark points of body parts in the subject 71 with a slice center position for the scan gantry 20 to achieve registration. Next, at Step S4, preparation for X-ray image capture is started. The control device 3 controls the gantry/table control section 29 here at Step S4 to perform preparation for X-ray image capture based on the imaging conditions loaded at Step S2.

The preparation for image capture involves bringing hardware constituting the X-ray CT apparatus 100 to a state ready to perform image capture. The control device 3 performs control to bring the X-ray emitting module 50, X-ray detector 27, and imaging table 10, for example, to a state ready to perform image capture.

Preparation for image capture for the X-ray emitting module 50 will be described hereinbelow. The control device 3 brings the X-ray tube 21, bow-tie filter module 23, and collimator 24 to a state ready for image capture. Preparation for image capture in the X-ray tube 21 includes, for example, rotation of the rotatable target electrode 21t, and selection of a cathode filament for use in image capture. Preparation for image capture in the bow-tie filter module 23 includes, for example, selection of a bow-tie filter for use in image capture. Preparation for image capture in the collimator 24 involves, for example, movement of the collimator 24 to provide the aperture of a size in image capture.

Moreover, in the case that a scout image is to be captured as the X-ray image, preparation for a scout scan is performed. The scout scan is imaging for capturing a scout image by emitting X-rays onto the subject 71 moved in the bore 20a by the cradle 12 while the X-ray emitting module 50 and X-ray detector 27 are fixed at a required position. Therefore, preparation for the scout scan may include disposing the X-ray emitting module 50 and X-ray detector 27 at a position required in performing the scout scan.

Furthermore, in the case that an X-ray CT tomographic image is to be captured as the X-ray image, preparation for a main scan is performed. The main scan is imaging for capturing an X-ray CT tomographic image by emitting radiation while the X-ray emitting module 50 and X-ray detector 27 are rotated around the subject 71 placed in the bore 20a. Therefore, preparation for the main scan may include rotating the X-ray emitting module 50 and X-ray detector 27 at a rotation speed in the main scan.

At Step S4, all or only some kinds of preparation for image capture described above may be performed.

Next, at Step S5, the operator decides whether or not to modify the imaging conditions loaded at Step S2. After being loaded from the storage device 7, the imaging conditions may be displayed on the monitor 6 or the touch panel in the gantry-side input device 30. The operator views the displayed imaging conditions and makes a decision.

When the operator decides to modify the imaging conditions at Step S5 ("YES" at Step S5), the flow goes to processing at Step S6. When the operator decides, on the other hand, not to modify the imaging conditions ("NO" at Step S5), the flow goes to processing at Step S7.

At Step S6, the operator performs an input for modifying the imaging conditions. The input may be performed on the input device 2 or gantry-side input device 30.

Next, at Step S8, the operator performs an input for confirming the imaging conditions at the input device 2 or gantry-side input device 30. The confirmation of the imaging conditions here at Step S8 includes confirmation of the imaging conditions modified at Step S6 and confirmation of the imaging conditions loaded at Step S2 and not modified at Step S6.

The input for confirming the imaging conditions at Step S8 and the input for modifying the imaging conditions at Step S6 represent an exemplary embodiment of the input of a result of a decision by the operator in the present invention.

Next, at Step S9 is started preparation for X-ray image capture based on the imaging conditions modified at Step S6. Specifically, the control device 3 controls the gantry/table control section 29 to perform preparation for X-ray image capture based on the imaging conditions input at Step S6. At Step S9 here, only preparation for image capture relating to the imaging conditions modified at Step S6 is started substituting for the preparation for image capture started at Step S4.

However, once the imaging conditions have been input at Step S6, preparation for image capture may be started before the input of confirmation is performed at Step S8.

On the other hand, when the operator decides that the imaging conditions do not have to be modified at Step S5, the operator performs an input for confirming the imaging conditions at the input device 2 or gantry-side input device 30 at Step S7. The confirmation of the imaging conditions at Step S7 is confirmation of the imaging conditions loaded at Step S2. The input of confirming the imaging conditions at Step S7 is an exemplary embodiment of the input of a result of a decision by the operator in the present invention.

Once the imaging conditions have been confirmed at Steps S7 and S8, X-ray image capture is performed at Step S10. Specifically, after the imaging conditions have been confirmed at Steps S7 and S8, and when preparation for image capture is completed, the condition is notified. To notify that preparation for image capture is completed, for example, an imaging start button constituting the input device 2 or gantry-side input device 30 lights up. When the operator presses the imaging start button, X-ray image capture at Step S10 is started.

Next, at Step S11, the control device 3 decides whether or not there is next image capture in the scan protocol set at Step S1. When it is decided that there is next image capture ("YES" at Step S11), the flow goes to Step S12. When it is decided, on the other hand, that there is no next image capture ("NO" at Step S11), the processing is terminated.

At Step S12, the control device 3 loads imaging conditions in image capture to be performed next in the scan protocol. The processing then goes back to Step S4, and the control device 3 controls the gantry/table control section 29 to perform preparation for image capture based on the imaging conditions loaded at Step S12.

According to the present embodiment described above, the control device 3 is configured to control several sections in the X-ray CT apparatus 100 to perform, before the input of the result of the decision by the operator as to whether or not to modify the imaging conditions loaded from the storage device 7, preparation for image capture based on the imaging conditions loaded from the storage device 7. Hence, time-consuming preparation for image capture can be started in an earlier phase, thus reducing the operator's wait time from the input of the result of the decision by the operator for the imaging conditions to when image capture is ready to start. Particularly, in the case that the imaging conditions loaded at Step S2 do not have to be modified and a confirmation input is performed at Step S7, the examination time can be reduced relative to the conventional case because preparation for image capture has already been started at Step S4. On the other hand, in the case that the imaging conditions are modified at Step S6, again, the examination time may be reduced relative to the conventional case because preparation for image capture relating to unmodified imaging conditions has already been performed.

Although preparation for image capture is started before the input of the result of the decision for the imaging conditions, in the case that modification of the imaging conditions is required, an input for modification may be performed after starting the preparation for image capture. The operator can thus set desired imaging conditions.

While the embodiment of the present invention has been described, the invention is not limited to the present embodiment and may be subjected to several modifications without departing from the spirit and scope thereof. For example, the invention is not limited to a case in which preparation for image capture is started when the input device 2 or gantry-side input device 30 has accepted an input by the operator. For example, in the case that the scan gantry 20 is provided with a camera for capturing an image of the subject 71, preparation for image capture may be started once the subject 71 has been recognized in an image captured by the camera. In this case, for example, preparation for image capture may be performed based on imaging conditions in a protocol selected immediately before, or in a facility in which the same protocol is always followed, preparation for image capture may be performed based on imaging conditions in the protocol. Moreover, preparation for image capture may be performed based on imaging conditions in a protocol depending upon the body part of the subject recognized in a camera image. Furthermore, preparation for image capture may be performed based on imaging conditions in a protocol selected by big data-based machine learning.

Figure 3:
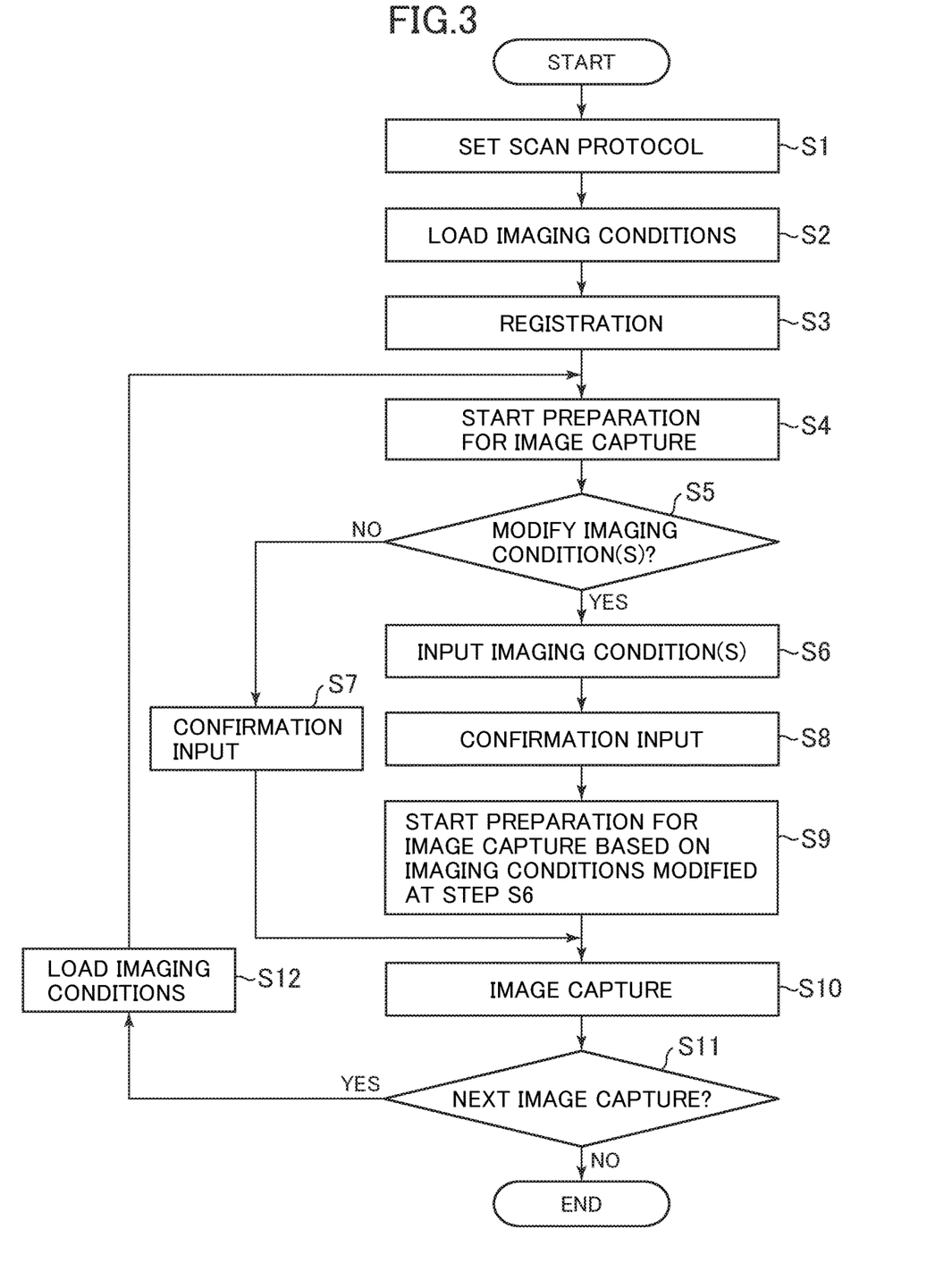
FIG. 3 illustrates a flow chart showing an exemplary operation of the X-ray CT apparatus in the embodiment.

Moreover, the flow chart shown in FIG. 3 is an example. Any flow in which the start of preparation for image capture is performed before the input device accepts the input of the result of the decision as to whether or not to modify imaging conditions is adequate. For example, registration may be performed before setting a scan protocol.

Furthermore, the preparation for image capture described in the embodiment above is an example. For example, as preparation for image capture, the gantry/table control section 29 may move the imaging table 10 to place the subject 71 at an imaging start position.

While the present embodiment is an X-ray CT apparatus, the invention is also applicable to tomographic imaging apparatuses using radiation other than X-rays, for example, those using gamma rays. Moreover, the invention is not limited to apparatuses for capturing a tomographic image.

We claim:

1. A system comprising:
    a storage device for storing therein imaging conditions for a radiographic image;
    a control device for controlling a radiographic imaging apparatus to perform a preparation for an image capture based on the imaging conditions loaded from the storage device; and
    an input device for accepting an input from an operator as to whether or not to modify the loaded imaging conditions after the radiographic imaging apparatus has started the preparation for the image capture.

2. The system of claim 1, wherein the radiographic imaging apparatus comprises at least one of a radiation emitting module for emitting radiation onto an object to be imaged, a radiation detector for detecting radiation emitted from the radiation emitting module, and an imaging table for placing thereon the object to be imaged, wherein:
the control device controls at least one of the radiation emitting module, the radiation detector, and the imaging table to perform the preparation for the image capture by bringing at least one of the radiation emitting module, the radiation detector, and the imaging table to a state ready for the image capture, and
the control device controls at least one of the radiation emitting module, the radiation detector, and the imaging table to bring at least one of the radiation emitting module, the radiation detector, and the imaging table to a state ready for the image capture.

3. The system of claim 2, wherein: the preparation for the image capture comprises bringing the radiation emitting module to a state ready for the image capture.

4. The system of claim 3, wherein:
the radiation emitting module comprises at least one of a radiation source, at least one bow-tie filter, and a collimator, and
the preparation for the image capture comprises bringing at least one of the radiation source, the at least one bow-tie filter, and the collimator to a state ready for the image capture.

5. The system of claim 4, wherein:
the radiation source comprises an X-ray tube,
the X-ray tube comprises a rotatable target electrode; and
the preparation for the image capture comprises rotating the rotatable target electrode.

6. The system of claim 5, wherein:
the X-ray tube further comprises a plurality of filaments, and
the preparation for the image capture comprises selecting one of the plurality of filaments for use in the image capture.

7. The system in claim 4, wherein:
the at least one bow-tie filter comprises a plurality of bow-tie filters, and
the preparation for the image capture comprises selecting one of the plurality of bow-tie filters for use in the image capture.

8. The system of claim 4, wherein:
the collimator is configured to form an aperture for limiting a range of a radiation impingement, and
the preparation for the image capture comprises moving the collimator to have the aperture of a size in the image capture.

9. The system of claim 3, wherein the radiographic imaging apparatus further comprises:
a gantry having a bore in which the object to be imaged can be placed, wherein
the radiation emitting module is housed in the gantry, and is configured to be able to emit radiation onto the object to be imaged placed in the bore and also to be rotatable around the object to be imaged placed in the bore,
the radiation detector is housed in the gantry, and is configured to detect radiation passing through the object to be imaged and also to be rotatable around the object to be imaged along with the radiation emitting module, and
the preparation for the image capture comprises at least one of rotating the radiation emitting module and the radiation detector, and disposing the radiation emitting module and the radiation detector at a position required in the image capture.

10. The system of claim 2, wherein the radiographic imaging apparatus further comprises:
a gantry having a bore in which the object to be imaged can be placed, wherein
the radiation emitting module is housed in the gantry, and is configured to be able to emit radiation onto the object to be imaged placed in the bore and also to be rotatable around the object to be imaged placed in the bore,
the radiation detector is housed in the gantry, and is configured to detect radiation passing through the object to be imaged and also to be rotatable around the object to be imaged along with the radiation emitting module, and
the preparation for the image capture comprises at least one of rotating the radiation emitting module and the radiation detector, and disposing the radiation emitting module and the radiation detector at a position required in the image capture.

11. The system of claim 10, wherein:
the radiographic image is a tomographic image of an object to be imaged obtained by emitting radiation onto the object to be imaged that is placed in the bore while the radiation emitting module and the radiation detector are rotating around the object to be imaged, or a scout image of an object to be imaged obtained by emitting radiation onto the object to be imaged that is moved within the bore while the radiation emitting module and the radiation detector are fixed at the required position.

12. The system of claim 1, wherein:
the input device accepts an input by the operator, the input being of an intention of performing a capture of the image on the object to be imaged,
the control device performs a control of the radiographic imaging apparatus to perform the preparation for the image capture.

13. The system of claim 12, wherein:
the input device accepts an input by the operator, the input being of an intention of performing a capture of the image on the object to be imaged,
the control device performs a control of the radiographic imaging apparatus to perform the preparation for the image capture after loading the imaging conditions from the storage device.

14. An imaging method comprising:
accepting a first input to capture a radiographic image of a subject;
in response to accepting the first input, loading imaging conditions for the radiographic image from a storage device;
controlling a radiographic imaging apparatus to perform a preparation for a radiographic image capture based on the loaded imaging conditions; and
after starting the preparation for the radiographic image capture, receiving a second input as to whether or not to modify the loaded imaging conditions.

15. The imaging method of claim 14, wherein the second input modifies loaded imaging conditions, the imaging method further comprising:
controlling the radiographic imaging apparatus to perform the perpetration for the radiographic image capture based on the modified loaded imaging conditions.

16. The imaging method of claim 14, wherein the radiographic imaging apparatus includes at least a radiation emitting module, a radiation detector, and an imaging table, and wherein the preparation for the radiographic image capture includes bringing at least one of the radiation emitting module, the radiation detector, and the imaging table to a state ready for the radiographic image capture.

17. The imaging method of claim 16, wherein the preparation for the radiographic image capture includes disposing the radiation emitting module and the radiation detector at a position for the radiographic image capture.

18. The imaging method of claim 16, wherein the radiation emitting module includes a radiation source, a bow-tie filter, and a collimator, and wherein the preparation for the radiographic image capture includes bringing at least one of the radiation source, the bow-tie filter, and the collimator to a state ready for the radiographic image capture.

19. The imaging method of claim 18, wherein the radiation source includes a target electrode, and wherein the preparation for the radiographic image capture includes rotating the target electrode.

20. The imaging method of claim 18, wherein the preparation for the radiographic image capture includes moving the collimator.

\* \* \* \* \*